United States Patent
Tang et al.

(10) Patent No.: US 11,168,049 B1
(45) Date of Patent: Nov. 9, 2021

(54) PLEUROMULIN TRETINOIN ESTER WITH ANTIBACTERIAL ACTIVITY AND A METHOD OF PREPARING THE SAME

(71) Applicants: Yonghong Tang, Xi'an (CN); Minghui Chang, Xi'an (CN); Huafeng Qi, Xi'an (CN); Bin Tian, Xi'an (CN); Juan Li, Xi'an (CN); Liang Xin, Xi'an (CN); Jingyi Li, Xi'an (CN); Dan Yang, Xi'an (CN); Han Li, Xi'an (CN); Yanjun Li, Xi'an (CN); Liang Qi, Xi'an (CN); Wenbo Yao, Xi'an (CN); Chengyuan Liang, Xi'an (CN)

(72) Inventors: Yonghong Tang, Xi'an (CN); Minghui Chang, Xi'an (CN); Huafeng Qi, Xi'an (CN); Bin Tian, Xi'an (CN); Juan Li, Xi'an (CN); Liang Xin, Xi'an (CN); Jingyi Li, Xi'an (CN); Dan Yang, Xi'an (CN); Han Li, Xi'an (CN); Yanjun Li, Xi'an (CN); Liang Qi, Xi'an (CN); Wenbo Yao, Xi'an (CN); Chengyuan Liang, Xi'an (CN)

(73) Assignee: XI'AN TAIKOMED PHARMACEUTICAL TECHNOLOGY CO., LTD., Xi'an (CN)

( * ) Notice: Subject to any disclaimer, the term of this patent is extended or adjusted under 35 U.S.C. 154(b) by 0 days.

(21) Appl. No.: 17/128,100

(22) Filed: Dec. 19, 2020

(51) Int. Cl.
*C07C 69/732* (2006.01)
*C07C 67/08* (2006.01)

(52) U.S. Cl.
CPC ........... *C07C 69/732* (2013.01); *C07C 67/08* (2013.01)

(58) Field of Classification Search
CPC .............................. C07C 67/732; C07C 69/08
See application file for complete search history.

(56) References Cited

U.S. PATENT DOCUMENTS

2012/0010281 A1* 1/2012 Sorensen ................ C07C 45/67
514/462

FOREIGN PATENT DOCUMENTS

GB            1111009 A  *  4/1968  ........... A23K 20/195

* cited by examiner

*Primary Examiner* — Yate' K Cutliff

(57) ABSTRACT

A compound with anti-drug resistant bacteria activity having the following formula (I):

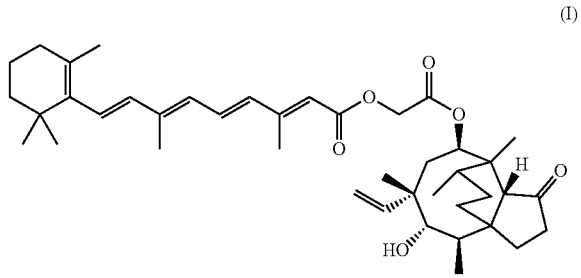

is disclosed. A method of preparing the compound of formula (I) is also disclosed.

16 Claims, 2 Drawing Sheets

PLEUROMULIN TRETINOIN ESTER WITH ANTIBACTERIAL ACTIVITY AND A METHOD OF PREPARING THE SAME

FIELD OF THE INVENTION

The present invention relates to the field of medicinal chemistry, and in particular, to a pleuromulin tretinoin easter with anti-drug-resistant-bacteria activity and a method of preparing the same.

BACKGROUND OF THE INVENTION

Multiple drug resistance refers to the simultaneous occurrence of resistance to a variety of commonly used antimicrobial agents, the main mechanism is the efflux membrane pump gene mutation, followed by the change of outer membrane permeability and the production of extended-spectrum enzymes. The most common gram-positive bacteria are multidrug resistant *Staphylococcus aureus* (MDR-MRSA), vancomycin-resistant *Enterococcus* (VRE) and *Streptococcus pneumoniae*, Gram-negative bacteria such as *Klebsiella pneumoniae*, *Escherichia coli* and non-fermentative bacteria *Acinetobacter baumannii* and *Pseudomonas aeruginosa*. Considering the increasing number of MDR, it is urgent to develop new anti-drug-resistant-bacteria drugs.

Pleuromulin (also known as Pleuromutilin) is a kind of broad-spectrum diterpene antibiotics produced by *Pleurotus mutilus*. It is composed of three rings and the most basic structure is an eight-membered ring. The carbonyl group on the five-membered ring and the hydroxyl group on C-11 are essential groups for activity. Pleuromulin antibiotics mainly act on the ribosome level of bacterial cells and block the synthesis of bacterial protein by inhibiting the activity of peptidyl transferase, thus achieving broad-spectrum antibacterial effect.

Tretinoin (also known as retinoic acid) is the metabolic intermediate of vitamin A, which mainly affects bone growth and epithelial metabolism, can promote the proliferation and renewal of epithelial cells, and can treat a variety of skin diseases. In addition, it also has the effects of anti-tumor, promoting wound healing and anti-infection, which is an important medical product.

The present invention modifies pleuromulin through tretinoin structure to obtain a pleuromulin tretinoin ester. The preliminary antibacterial activity experiment shows that the compound has excellent antibacterial activity and has high medical research and application value in the treatment of infectious diseases caused by multi-drug-resistant bacteria.

SUMMARY OF THE INVENTION

In one embodiment, the present application provides a pleuromulin tretinoin ester, i.e., a compound having the following formula (I):

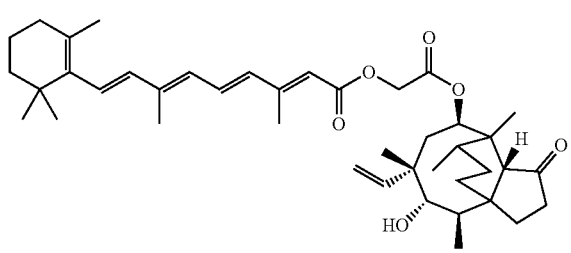

In another embodiment, the present application provides a method of preparing the compound of formula (I). The method includes reacting a compound of formula (II) (pleuromulin) with a compound of formula (III) (tretinoin) to obtain the compound of formula (I):

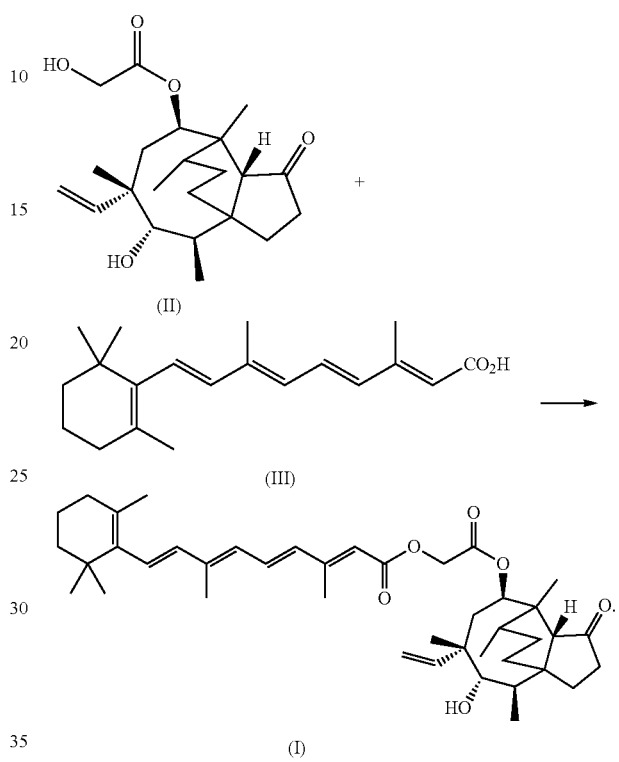

In another embodiment, the reaction of the compound of formula (II) with the compound of formula (III) comprises the following steps: placing the compound of formula (II) and the compound of formula (III), in a molar ratio of 1:1 to 1:1.3, in a reactor; adding an organic solvent and a catalytic amount of 4-DMAP (4-dimethylaminopyridine) under nitrogen atmosphere to obtain a reaction mixture; stirring the reaction mixture at 0° C. for five minutes and then adding DCC (N,N'-dicyclohexylcarbodiimide) to the reaction mixture; stirring the reaction mixture in dark at 20-40° C. for 3 to 5 hours; concentrating the reaction mixture and extracting with ethyl acetate to obtain a crude product; and purifying the crude product on a silica gel fresh chromatography column with petroleum ether and ethyl acetate with a ratio of 1:1 to 4:1 as an eluent to obtain the compound of formula (I).

In another embodiment, the organic solvent is toluene, dichloromethane or DMF.

In another embodiment, the organic solvent is dichloromethane.

In another embodiment, the molar ratio of the compound of formula (II) and the compound of formula (III) is 1:1.2.

In another embodiment, the reaction mixture is stirred in dark at 30° C.

In another embodiment, the reaction mixture is stirred for 4 hours.

In another embodiment, the eluent is petroleum ether: ethyl acetate=3:1.

In another embodiment, the reaction of the compound of formula (II) with the compound of formula (III) comprises the following steps: placing the compound of formula (II), a catalyst, and an ionic liquid in a reactor under nitrogen atmosphere, the catalyst being 12-molybdosilicic acid hydrate ($H_6Mo_{12}O_{41}Si$); adding the compound of formula (III) to the reactor to form a reaction mixture; heating the reaction mixture at 20-40° C. for 2-6 hours; placing the reaction mixture in a separating funnel to separate a crude product; purifying the crude product by recrystallization in methanol to obtain the compound of formula (I); and recycling the ionic liquid.

In another embodiment, the ionic liquid is 1-ethyl-3-methylimidazolium tetrachloroferrate ($C_6H_{11}Cl_4FeN_2$), 1-hexyl-3-methylimidazolium tetrafluoroborate, or 1-butyl-3-methylimi-dazolium tetrafluoroborate.

In another embodiment, the ionic liquid is the ionic liquid is 1-ethyl-3-methylimidazolium tetrachloroferrate ($C_6H_{11}Cl_4FeN_2$).

In another embodiment, the compound of formula (II) and the compound (III) have a molar ratio of 1:1 to 1:1.3.

In another embodiment, the molar ratio of the compound of formula (II) and the compound of formula (III) is 1:1.1.

In another embodiment, the reaction mixture is heated at 20° C.

In another embodiment, the reaction mixture is heated for 6 hours.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
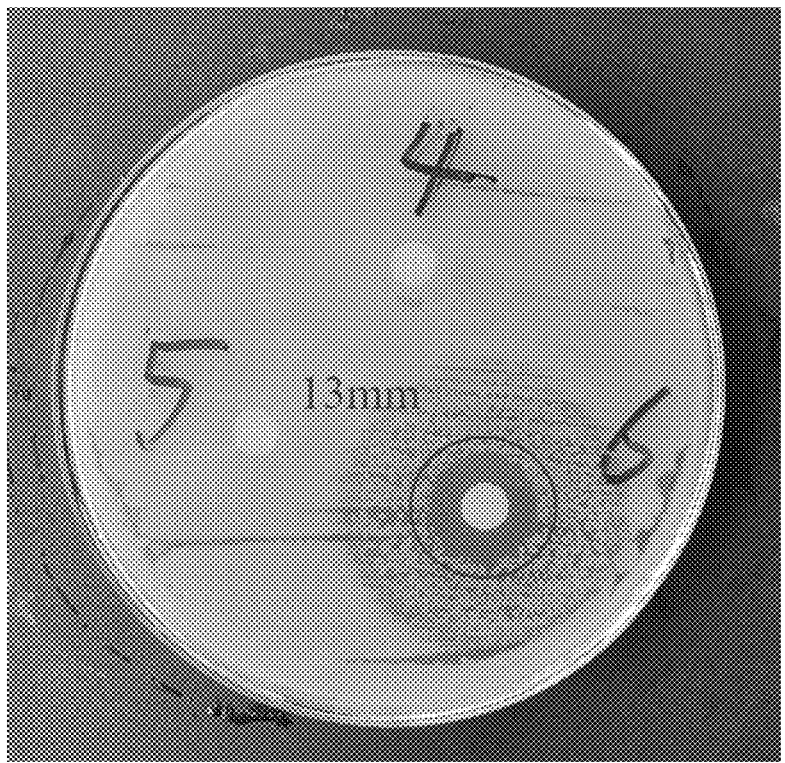
FIG. 1 shows the in vitro antibacterial activity of the pleuromulin tretinoin ester against drug-resistant bacteria MRSA 206.

Reference will now be made in detail to embodiments of the present invention, example of which is illustrated in the accompanying drawings. The following examples illustrate the present invention, but the present invention is not limited to the following examples.

Example 1

Preparation of the pleuromulin tretinoin ester ((2E,4E,6E,8E)-2-(((4R,5S,6 S,8R,9aR)-5-hydroxy-4,6,9,10-tetramethyl-1-oxo-6-vinyldecahydro-3a,9-propanocyclopenta[8]annulen-8-yl)oxy)-2-oxoethyl 3,7-dimethyl-9-(2,6,6-trimethylcyclohex-1-en-1-yl) nona-2,4,6,8-tetraenoate)

In a 100 mL three-necked flask, 378.5 mg (1.00 mmol) of pleuromulin and 3.7 mg (0.03 mmol) 4-DMAP were dissolved in 30 mL of dichloromethane under nitrogen atmosphere. 360.5 mg (1.20 mmol) of tretinoin was dissolved in 30 mL of dichloromethane, and added dropwise to the reaction mixture by a separatory funnel. After the completion of the dropwise addition, the reaction mixture was stirred for 5 minutes at 0° C., and 206.3 mg (1.00 mmol) of shrinking agent DCC was then added. The reaction mixture was removed from the ice bath, and the reaction was reacted in dark (shielded from light) at 30° C. for 4 hours. Thin layer chromatography was used to track the reaction to completion. The reaction mixture was concentrated, washed with water, extracted with ethyl acetate, dried and concentrated to obtain a crude product. The crude product was purified by silica gel column chromatography, eluting with petroleum ether:ethyl acetate=3:1 as eluent, and the eluent containing the product was combined, concentrated under reduced pressure, and dried to obtain 485.60 mg of the pleuromulin tretinoin ester, a total yield of 72.16%.

$^1$H-NMR (400 MHz, chloroform-d) δ (ppm): 7.08 (1H, d), 6.37 (1H, d), 6.21 (2H, d), 6.17 (2H, m), 5.83 (2H, s), 5.28 (2H, m), 4.67 (1H, d), 4.53 (1H, d), 3.41 (1H, d), 2.40 (1H, m), 2.27 (1H, s), 2.13 (6H, m), 2.01 (2H, t), 1.83-1.58 (13H, t), 1.48-1.39 (9H, t), 1.22 (6H, s), 1.08 (3H, s), 0.93 (3H, d), 0.83 (3H, d); $^{13}$C-NMR (400 MHz, chloroform-d) δ (ppm): 216.9, 167.2, 165.9, 154.6, 140.1, 134.8, 130.1, 129.0, 117.3, 116.9, 74.6, 69.5, 60.8, 58.1, 45.4, 44.6, 44.0, 41.9, 39.6, 36.7, 33.1, 28.9, 26.4, 24.8, 21.7, 19.2, 16.6, 14.8, 14.0, 12.9, 11.41.

Example 2

Preparation of the Pleuromulin Tretinoin Ester

In a 100 mL three-necked flask, 378.5 mg (1.00 mmol) of pleuromulin and 3.7 mg (0.03 mmol) 4-DMAP were dissolved in 30 mL of dichloromethane under nitrogen atmosphere. 390.6 mg (1.30 mmol) of tretinoin was dissolved in 30 mL of dichloromethane, and added dropwise to the reaction mixture by a separatory funnel. After the completion of the dropwise addition, the reaction mixture was stirred for 5 minutes at 0° C., and 206.3 mg (1.00 mmol) of shrinking agent DCC was then added. The reaction mixture was removed from the ice bath, and the reaction was reacted in dark (shielded from light) at 20° C. for 3 hours. Thin layer chromatography was used to track the reaction to completion. The reaction mixture was concentrated, washed with water, extracted with ethyl acetate, dried and concentrated to obtain a crude product. The crude product was purified by silica gel column chromatography, eluting with petroleum ether:ethyl acetate=2:1 as eluent, and the eluent containing the product was combined, concentrated under reduced pressure, and dried to obtain 451.68 mg of the pleuromulin tretinoin ester, a total yield of 67.12%.

Example 3

Preparation of the Pleuromulin Tretinoin Ester

In a 100 mL three-necked flask, 378.5 mg (1.00 mmol) of pleuromulin and 3.7 mg (0.03 mmol) 4-DMAP were dissolved in 30 mL of dichloromethane under nitrogen atmosphere. 330.5 mg (1.10 mmol) of tretinoin was dissolved in 30 mL of dichloromethane, and added dropwise to the reaction mixture by a separatory funnel. After the completion of the dropwise addition, the reaction mixture was stirred for 5 minutes at 0° C., and 206.3 mg (1.00 mmol) of shrinking agent DCC was then added. The reaction mixture was removed from the ice bath, and the reaction was reacted in dark (shielded from light) at 30° C. for 5 hours. Thin layer chromatography was used to track the reaction to completion. The reaction mixture was concentrated, washed with water, extracted with ethyl acetate, dried and concentrated to obtain a crude product. The crude product was purified by silica gel column chromatography, eluting with petroleum ether:ethyl acetate=1:1 as eluent, and the eluent containing the product was combined, concentrated under reduced pressure, and dried to obtain 462.34 mg of the pleuromulin tretinoin ester, a total yield of 68.70%.

Example 4

Preparation of the Pleuromulin Tretinoin Ester

In a 100 mL three-necked flask, 378.5 mg (1.00 mmol) of pleuromulin and 3.7 mg (0.03 mmol) 4-DMAP were dissolved in 30 mL of dichloromethane under nitrogen atmosphere. 360.4 mg (1.20 mmol) of tretinoin was dissolved in 30 mL of dichloromethane, and added dropwise to the reaction mixture by a separatory funnel. After the completion of the dropwise addition, the reaction mixture was stirred for 5 minutes at 0° C., and 206.3 mg (1.00 mmol) of shrinking agent DCC was then added. The reaction mixture was removed from the ice bath, and the reaction was reacted in dark (shielded from light) at 30° C. for 3 hours. Thin layer chromatography was used to track the reaction to completion. The reaction mixture was concentrated, washed with water, extracted with ethyl acetate, dried and concentrated to obtain a crude product. The crude product was purified by silica gel column chromatography, eluting with petroleum ether:ethyl acetate=2:1 as eluent, and the eluent containing the product was combined, concentrated under reduced pressure, and dried to obtain 463.49 mg of the pleuromulin tretinoin ester, a total yield of 68.73%.

Example 5

Preparation of the Pleuromulin Tretinoin Ester

In a 100 mL three-necked flask, 378.5 mg (1.00 mmol) of pleuromulin and 3.7 mg (0.03 mmol) 4-DMAP were dissolved in 30 mL of dichloromethane under nitrogen atmosphere. 390.6 mg (1.30 mmol) of tretinoin was dissolved in 30 mL of dichloromethane, and added dropwise to the reaction mixture by a separatory funnel. After the completion of the dropwise addition, the reaction mixture was stirred for 5 minutes at 0° C., and 206.3 mg (1.00 mmol) of shrinking agent DCC was then added. The reaction mixture was removed from the ice bath, and the reaction was reacted in dark (shielded from light) at 30° C. for 3 hours. Thin layer chromatography was used to track the reaction to completion. The reaction mixture was concentrated, washed with water, extracted with ethyl acetate, dried and concentrated to obtain a crude product. The crude product was purified by silica gel column chromatography, eluting with petroleum ether:ethyl acetate=1:1 as eluent, and the eluent containing the product was combined, concentrated under reduced pressure, and dried to obtain 453.74 mg of the pleuromulin tretinoin ester, a total yield of 67.43%.

Example 6

Preparation of the Pleuromulin Tretinoin Ester

In a 100 mL three-necked flask, 378.5 mg (1.00 mmol) of pleuromulin and 3.7 mg (0.03 mmol) 4-DMAP were dissolved in 30 mL of dichloromethane under nitrogen atmosphere. 330.5 mg (1.10 mmol) of tretinoin was dissolved in 30 mL of dichloromethane, and added dropwise to the reaction mixture by a separatory funnel. After the completion of the dropwise addition, the reaction mixture was stirred for 5 minutes at 0° C., and 206.3 mg (1.00 mmol) of shrinking agent DCC was then added. The reaction mixture was removed from the ice bath, and the reaction was reacted in dark (shielded from light) at 30° C. for 4 hours. Thin layer chromatography was used to track the reaction to completion. The reaction mixture was concentrated, washed with water, extracted with ethyl acetate, dried and concentrated to obtain a crude product. The crude product was purified by silica gel column chromatography, eluting with petroleum ether:ethyl acetate=1:1 as eluent, and the eluent containing the product was combined, concentrated under reduced pressure, and dried to obtain 467.49 mg of the pleuromulin tretinoin ester, a total yield of 69.47%.

Example 7

Preparation of the Pleuromulin Tretinoin Ester

In a 100 mL three-necked flask, 378.5 mg (1.00 mmol) of pleuromulin and 3.7 mg (0.03 mmol) 4-DMAP were dissolved in 30 mL of dichloromethane under nitrogen atmosphere. 330.5 mg (1.10 mmol) of tretinoin was dissolved in 30 mL of dichloromethane, and added dropwise to the reaction mixture by a separatory funnel. After the completion of the dropwise addition, the reaction mixture was stirred for 5 minutes at 0° C., and 206.3 mg (1.00 mmol) of shrinking agent DCC was then added. The reaction mixture was removed from the ice bath, and the reaction was reacted in dark (shielded from light) at 40° C. for 3 hours. Thin layer chromatography was used to track the reaction to completion. The reaction mixture was concentrated, washed with water, extracted with ethyl acetate, dried and concentrated to obtain a crude product. The crude product was purified by silica gel column chromatography, eluting with petroleum ether:ethyl acetate=1:1 as eluent, and the eluent containing the product was combined, concentrated under reduced pressure, and dried to obtain 441.29 mg of the pleuromulin tretinoin ester, a total yield of 65.58%.

Example 8

Preparation of the Pleuromulin Tretinoin Ester

In a 100 mL three-necked flask, 378.5 mg (1.00 mmol) of pleuromulin and 3.7 mg (0.03 mmol) 4-DMAP were dissolved in 30 mL of dichloromethane under nitrogen atmosphere. 390.6 mg (1.30 mmol) of tretinoin was dissolved in 30 mL of dichloromethane, and added dropwise to the reaction mixture by a separatory funnel. After the completion of the dropwise addition, the reaction mixture was stirred for 5 minutes at 0° C., and 206.3 mg (1.00 mmol) of shrinking agent DCC was then added. The reaction mixture was removed from the ice bath, and the reaction was reacted in dark (shielded from light) at 20° C. for 4 hours. Thin layer chromatography was used to track the reaction to completion. The reaction mixture was concentrated, washed with water, extracted with ethyl acetate, dried and concentrated to obtain a crude product. The crude product was purified by silica gel column chromatography, eluting with petroleum ether:ethyl acetate=2:1 as eluent, and the eluent containing the product was combined, concentrated under reduced pressure, and dried to obtain 444.36 mg of the pleuromulin tretinoin ester, a total yield of 66.03%.

Example 9

Preparation of the Pleuromulin Tretinoin Ester

In a 100 mL three-necked flask, 378.5 mg (1.00 mmol) of pleuromulin and 3.7 mg (0.03 mmol) 4-DMAP were dissolved in 30 mL of dichloromethane under nitrogen atmosphere. 330.5 mg (1.10 mmol) of tretinoin was dissolved in 30 mL of dichloromethane, and added dropwise to the reaction mixture by a separatory funnel. After the completion of the dropwise addition, the reaction mixture was stirred for 5 minutes at 0° C., and 206.3 mg (1.00 mmol) of shrinking agent DCC was then added. The reaction mixture was removed from the ice bath, and the reaction was reacted in dark (shielded from light) at 20° C. for 5 hours. Thin layer chromatography was used to track the reaction to completion. The reaction mixture was concentrated, washed with water, extracted with ethyl acetate, dried and concentrated to obtain a crude product. The crude product was purified by silica gel column chromatography, eluting with petroleum ether:ethyl acetate=4:1 as eluent, and the eluent containing the product was combined, concentrated under reduced pressure, and dried to obtain 435.68 mg of the pleuromulin tretinoin ester, a total yield of 64.74%.

Example 10

Preparation of the Pleuromulin Tretinoin Ester

In a 100 mL three-necked flask, 378.5 mg (1.00 mmol) of pleuromulin and 3.7 mg (0.03 mmol) 4-DMAP were dissolved in 30 mL of dichloromethane under nitrogen atmosphere. 360.5 mg (1.20 mmol) of tretinoin was dissolved in 30 mL of dichloromethane, and added dropwise to the reaction mixture by a separatory funnel. After the completion of the dropwise addition, the reaction mixture was stirred for 5 minutes at 0° C., and 206.3 mg (1.00 mmol) of shrinking agent DCC was then added. The reaction mixture was removed from the ice bath, and the reaction was reacted in dark (shielded from light) at 40° C. for 4 hours. Thin layer chromatography was used to track the reaction to completion. The reaction mixture was concentrated, washed with water, extracted with ethyl acetate, dried and concentrated to obtain a crude product. The crude product was purified by silica gel column chromatography, eluting with petroleum ether:ethyl acetate=4:1 as eluent, and the eluent containing the product was combined, concentrated under reduced pressure, and dried to obtain 437.26 mg of the pleuromulin tretinoin ester, a total yield of 64.98%.

Example 11

Preparation of the Pleuromulin Tretinoin Ester

In a 100 mL three-necked flask, 378.5 mg (1.00 mmol) of pleuromulin and 3.7 mg (0.03 mmol) 4-DMAP were dissolved in 30 mL of dichloromethane under nitrogen atmosphere. 390.6 mg (1.30 mmol) of tretinoin was dissolved in 30 mL of dichloromethane, and added dropwise to the reaction mixture by a separatory funnel. After the completion of the dropwise addition, the reaction mixture was stirred for 5 minutes at 0° C., and 206.3 mg (1.00 mmol) of shrinking agent DCC was then added. The reaction mixture was removed from the ice bath, and the reaction was reacted in dark (shielded from light) at 30° C. for 5 hours. Thin layer chromatography was used to track the reaction to completion. The reaction mixture was concentrated, washed with water, extracted with ethyl acetate, dried and concentrated to obtain a crude product. The crude product was purified by silica gel column chromatography, eluting with petroleum ether:ethyl acetate=2:1 as eluent, and the eluent containing the product was combined, concentrated under reduced pressure, and dried to obtain 449.54 mg of the pleuromulin tretinoin ester, a total yield of 66.80%.

Example 12

Preparation of the Pleuromulin Tretinoin Ester

In a 250 mL three-necked flask, 378.5 mg (1.00 mmol) of pleuromulin, 330.5 mg (1.10 mmol) of tretinoin, and 20.3 mg (0.011 mmol) silicomolybdic acid were dissolved in 100 mL of 1-ethyl-3-methylimidazolium tetrachloroferrate under nitrogen atmosphere. After full dissolution, the temperature of the reaction mixture was raised to 20° C. and the reaction was carried out for 4 hours. Thin layer chromatography was used to track the reaction to completion, heating was stopped, and the protective device was removed. The reaction mixture was allowed to separate into layers to obtain a crude product. The crude product was recrystallized with 50 mL methanol and dried to obtain 568.2 mg of the pleuromulin tretinoin ester, a total yield of 86.03%.

Example 13

Preparation of the Pleuromulin Tretinoin Ester

In a 250 mL three-necked flask, 378.5 mg (1.00 mmol) of pleuromulin, 330.5 mg (1.10 mmol) of tretinoin, and 20.3 mg (0.011 mmol) silicomolybdic acid were dissolved in 100 mL of 1-butyl-3-methylimidazolium tetrafluoroborate under nitrogen atmosphere. After full dissolution, the temperature of the reaction mixture was raised to 30° C. and the reaction was carried out for 4 hours. Thin layer chromatography was used to track the reaction to completion, heating was stopped, and the protective device was removed. The reaction mixture was allowed to separate into layers to obtain a crude product. The crude product was recrystallized with 50 mL methanol and dried to obtain 536.6 mg of the pleuromulin tretinoin ester, a total yield of 81.25%.

Example 14

Preparation of the Pleuromulin Tretinoin Ester

In a 250 mL three-necked flask, 378.5 mg (1.00 mmol) of pleuromulin, 330.5 mg (1.10 mmol) of tretinoin, and 20.3 mg (0.011 mmol) silicomolybdic acid were dissolved in 100 mL of 1-hexyl-3-methylimidazolium tetrafluoroborate under nitrogen atmosphere. After full dissolution, the temperature of the reaction mixture was raised to 40° C. and the reaction was carried out for 2 hours. Thin layer chromatography was used to track the reaction to completion, heating was stopped, and the protective device was removed. The reaction mixture was allowed to separate into layers to obtain a crude product. The crude product was recrystallized with 50 mL methanol and dried to obtain 535.2 mg of the pleuromulin tretinoin ester, a total yield of 82.55%.

Example 15

Preparation of the Pleuromulin Tretinoin Ester

In a 250 mL three-necked flask, 378.5 mg (1.00 mmol) of pleuromulin, 330.5 mg (1.10 mmol) of tretinoin, and 20.3 mg (0.011 mmol) silicomolybdic acid were dissolved in 100 mL of 1-ethyl-3-methylimidazolium tetrachloroferrate under nitrogen atmosphere. After full dissolution, the temperature of the reaction mixture was raised to 25° C. and the reaction was carried out for 5 hours. Thin layer chromatography was used to track the reaction to completion, heating was stopped, and the protective device was removed. The reaction mixture was allowed to separate into layers to obtain a crude product. The crude product was recrystallized with 50 mL methanol and dried to obtain 559.8 mg of the pleuromulin tretinoin ester, a total yield of 84.76%.

Example 16

Antibacterial Activity Test of the Compounds of the Invention

The antimicrobial efficacy was determined by a paper diffusion drug sensitivity test.

Experimental strains: multi-resistant *Staphylococcus aureus* 206, multi-resistant *Staphylococcus aureus* 575, multi-resistant *Staphylococcus aureus* 596. The experimental strain was identified by Huashan Hospital Affiliated to Fudan University (Institute of Antibiotic of Fudan University).

Drug sensitive paper: the drug sensitive paper is a special drug sensitive paper with a diameter of 6.35 mm and a water absorption of 0.02 mL. The control drug was vancomycin (30 μg/tablet); the test drugs were pleuromulin (30 μg/tablet), tretinoin (30 μg/tablet) and the pleuromulin tretinoin ester (30 μg/tablet).

Reagents: LB agar medium, LA broth medium, 0.5% DMSO solution.

Equipment: Ultra-clean workbench, high-pressure sterilization pot, gas bath constant temperature shaking incubator.

Preparation of Bacterial Suspension:

The experimental strains were inoculated in non-selective medium and placed in air at 37° C. for 24 h, picking a single colony that grows well and inoculating it into broth medium, incubating at 35° C.±2° C. for 6 hours, and using LA broth medium to calibrate the concentration of the bacterial solution to 0.5 Mie turbidimetric tube ($1.5 \times 10^8$ CFU/mL). A bacterial suspension is obtained.

Paper Diffusion Method Drug Sensitivity Test:

Weigh the LB dry powder, sterilize at 103.4 Kpa, 121.3° C. high-pressure steam for 15 min, and then put it in a 40° C.-50° C. water bath. Place a sterile empty plate (inner diameter 9 cm) on the surface of the ultra-clean table water table, shake the LB, and then pour the plate. The thickness of each plate is 3 mm to 4 mm. After the plate was cooled at room temperature, storing it in the refrigerator at 2° C.-8° C., using a sterile cotton swab to dip the bacterial solution, and evenly coating the surface of the LB plate 3 times. After inoculation of the bacterial suspension, the LB plate was dried at room temperature for 3 min to 5 min. Use sterile forceps to closely attach the antibacterial drug paper to the dish. Put the dish upside down and place it in a 37° C. incubator for 24 h. Observe the result and measure the diameter. Taking 0.5% DMSO solution as a negative control, the antibacterial activity was expressed by the diameter of the inhibition zone. The inhibition zone≥17 mm, sensitive; the inhibition zone is 15 mm-16 mm, intermediary; the inhibition zone≤14 mm, drug resistance.

Figure 2:
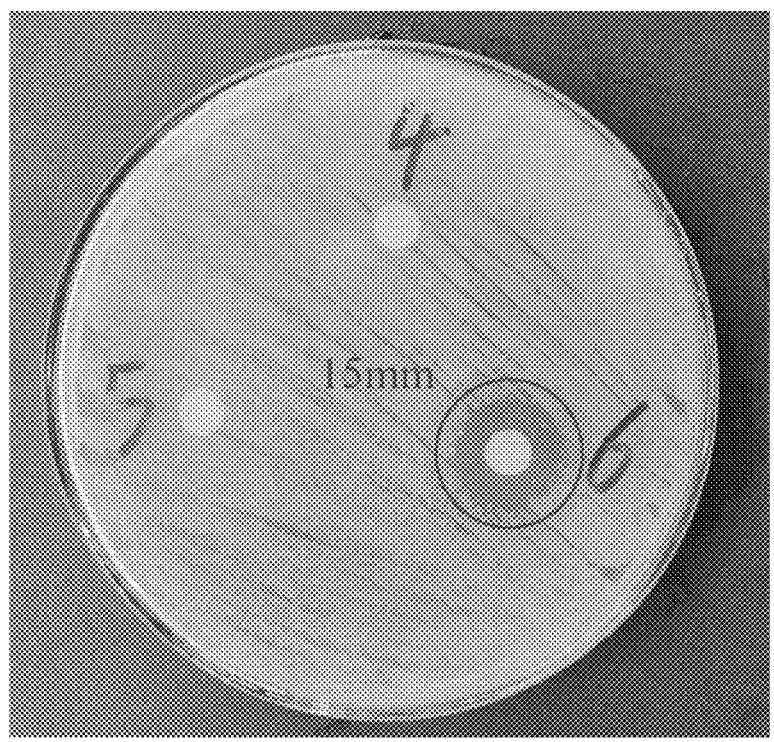
FIG. 2 shows the in vitro antibacterial activity of the pleuromulin tretinoin ester against drug-resistant bacteria MRSA 596.
Figure 3:
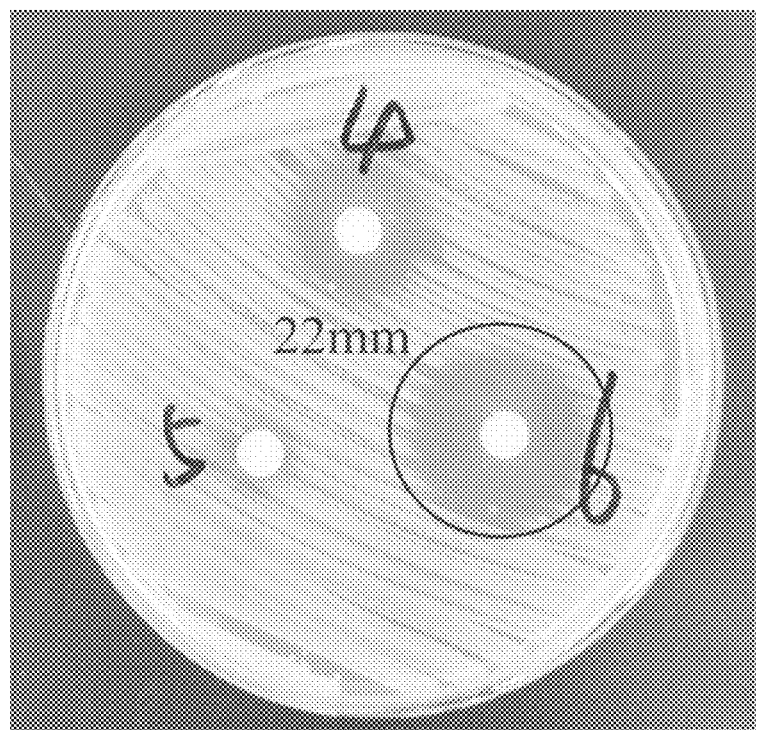
FIG. 3 shows the in vitro antibacterial activity of the pleuromulin tretinoin ester against drug-resistant bacteria MRSA 575.

In FIGS. 1-3, the pleuromulin tretinoin ester is represented by the number six. FIG. 1 shows the antibacterial effect of pleuromulin tretinoin ester on MRSA-206. FIG. 2 shows the antibacterial effect of pleuromulin tretinoin ester on MRSA-575. FIG. 3 shows the antibacterial effect of pleuromulin tretinoin ester on MRSA-596. The results are shown in Table 1.

TABLE 1

Experimental results of the zone of inhibition

| Compound | Zone of inhibition/mm Strain | | |
|---|---|---|---|
| | MRSA-206 | MRSA-575 | MRSA-596 |
| 0.5% DMSO | 0 | 0 | 0 |
| Vancomycin | 15 | 17 | 23 |
| Pleuromulin | 0 | 0 | 0 |
| Tretinoin | 0 | 0 | 0 |
| Pleuromulin tretinoin ester | 13 | 15 | 22 |

The results in FIGS. 1-3 and Table 1 show that the starting materials pleuromutilin and tretinoin have no inhibitory effect on drug-resistant bacteria. Pleuromutilin tretinoin ester has strong inhibitory effects on multi-drug resistant *Staphylococcus aureus* 206, 575, 596, and the diameter of bacteriostatic zone against multidrug resistant *Staphylococcus aureus* 596 was up to 22 mm. In summary, the pleuromutilin tretinoin ester of the present invention can be used as an antibacterial drug candidate for multi-drug resistant *Staphylococcus aureus*, and further preclinical studies will be conducted.

What is claimed is:

1. A compound having the following formula (I):

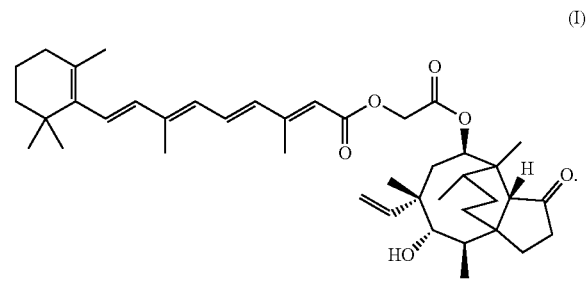 [SMILES: C=C[C@]1(C)C[C@@H](OC(=O)COC(=O)/C=C(C)/C=C/C=C(C)/C=C/C2=C(C)CCCC2(C)C)C2(C)C(C)CCC3(CCC(=O)[C@H]32)[C@@H](C)[C@@H]1O]

(I)

2. A method of preparing the compound of formula (I) of claim 1, comprising: reacting a compound of formula (II) with a compound of formula (III) to obtain the compound of formula (I):

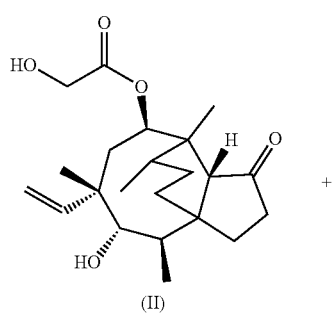

(II)

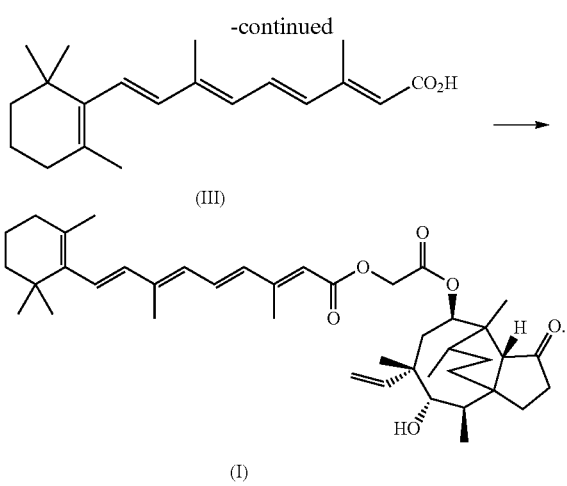

3. The method of claim 2, wherein the reaction of the compound of formula (II) with the compound of formula (III) comprises the following steps:
placing the compound of formula (II) and the compound of formula (III), in a molar ratio of 1:1 to 1:1.3, in a reactor;
adding an organic solvent and a catalytic amount of 4-DMAP (4-dimethylaminopyridine) under nitrogen atmosphere to obtain a reaction mixture;
stirring the reaction mixture at 0° C. for five minutes and then adding DCC (N,N'-dicyclohexylcarbodiimide) to the reaction mixture;
stirring the reaction mixture in dark at 20-40° C. for 3 to 5 hours;
concentrating the reaction mixture and extracting with ethyl acetate to obtain a crude product; and
purifying the crude product on a silica gel fresh chromatography column with petroleum ether and ethyl acetate with a ratio of 1:1 to 4:1 as an eluent to obtain the compound of formula (I).

4. The method of claim 3, wherein the organic solvent is toluene, dichloromethane or DMF.

5. The method of claim 4, wherein the organic solvent is dichloromethane.

6. The method of claim 3, wherein the molar ratio of the compound of formula (II) and the compound of formula (III) is 1:1.2.

7. The method of claim 3, wherein the reaction mixture is stirred in dark at 30° C.

8. The method of claim 7, wherein the reaction mixture is stirred for 4 hours.

9. The method of claim 3, wherein the eluent is petroleum ether:ethyl acetate=3:1.

10. The method of claim 2, wherein the reaction of the compound of formula (II) with the compound of formula (III) comprises the following steps:
placing the compound of formula (II), a catalyst, and an ionic liquid in a reactor under nitrogen atmosphere, the catalyst being 12-molybdosilicic acid hydrate ($H_6Mo_{12}O_{41}Si$);
adding the compound of formula (III) to the reactor to form a reaction mixture;
heating the reaction mixture at 20-40° C. for 2-6 hours;
placing the reaction mixture in a separating funnel to separate a crude product;
purifying the crude product by recrystallization in methanol to obtain the compound of formula (I); and
recycling the ionic liquid.

11. The method of claim 10, wherein the ionic liquid is 1-ethyl-3-methylimidazolium tetrachloroferrate ($C_6H_{11}Cl_4FeN_2$), 1-hexyl-3-methylimidazolium tetrafluoroborate, or 1-butyl-3-methylimidazolium tetrafluoroborate.

12. The method of claim 11, wherein the ionic liquid is the ionic liquid is 1-ethyl-3-methylimidazolium tetrachloroferrate ($C_6H_{11}Cl_4FeN_2$).

13. The method of claim 10, wherein the compound of formula (II) and the compound (III) have a molar ratio of 1:1 to 1:1.3.

14. The method of claim 13, wherein the molar ratio of the compound of formula (II) and the compound of formula (III) is 1:1.1.

15. The method of claim 10, wherein the reaction mixture is heated at 20° C.

16. The method of claim 10, wherein the reaction mixture is heated for 6 hours.

* * * * *